US008623641B2

(12) United States Patent
Chen et al.

(10) Patent No.: US 8,623,641 B2
(45) Date of Patent: Jan. 7, 2014

(54) APPARATUS AND METHOD FOR WASHING BIOLOGICAL MATERIAL

(75) Inventors: Chung-Nun Chen, Taichung County (TW); Chun-Jen Liao, Taipei (TW); Chin-Yu Lin, Chia-Yi County (TW); Chin-Fu Chen, Taipei County (TW); Yung-chih Wu, Taipei County (TW)

(73) Assignee: Industrial Technology Research Institute (TW)

( * ) Notice: Subject to any disclaimer, the term of this patent is extended or adjusted under 35 U.S.C. 154(b) by 1559 days.

(21) Appl. No.: 12/104,685

(22) Filed: Apr. 17, 2008

(65) Prior Publication Data

US 2009/0007937 A1     Jan. 8, 2009

(51) Int. Cl.
| C12M 1/00 | (2006.01) |
| C12M 3/00 | (2006.01) |
| B01L 3/02 | (2006.01) |
| G01N 21/75 | (2006.01) |
| G01N 31/22 | (2006.01) |
| G01N 33/52 | (2006.01) |
| G01N 1/14 | (2006.01) |
| G01N 1/22 | (2006.01) |

(52) U.S. Cl.
USPC ............... 435/307.1; 435/283.1; 422/422; 422/513; 73/864; 73/864.16

(58) Field of Classification Search
USPC ............... 435/307.1, 283.1–309.4; 73/864, 73/864.16; 422/500–570, 400–430
See application file for complete search history.

(56) References Cited

U.S. PATENT DOCUMENTS

| 1,386,340 A | 8/1921 | Wuster |
| 3,481,477 A | 12/1969 | Farr |
| 3,870,639 A | 3/1975 | Moore et al. |
| 5,330,916 A * | 7/1994 | Williams et al. ............ 435/286.4 |
| 5,549,816 A | 8/1996 | Harp et al. |
| 5,552,325 A * | 9/1996 | Nochumson et al. .......... 436/177 |
| 5,663,051 A | 9/1997 | Vlasselaer |
| 5,932,174 A * | 8/1999 | Brayton et al. ................. 422/79 |
| 5,976,824 A | 11/1999 | Gordon |
| 6,123,687 A | 9/2000 | Simonyi et al. |
| 6,221,655 B1 * | 4/2001 | Fung et al. ................. 435/288.1 |
| 6,521,190 B1 | 2/2003 | Edens et al. |
| 2004/0184966 A1 * | 9/2004 | Zhou et al. .................... 422/102 |

FOREIGN PATENT DOCUMENTS

| CN | 2208975 Y | 10/1995 |
| DE | 3542331 | 6/1987 |
| EP | 0325910 B1 | 9/1993 |
| EP | 737443 A2 * | 10/1996 |
| WO | WO02/060556 | 8/2002 |

* cited by examiner

*Primary Examiner* — Nathan Bowers
*Assistant Examiner* — Lydia Edwards
(74) *Attorney, Agent, or Firm* — Cesari and McKenna, LLP

(57) ABSTRACT

In a general aspect, an apparatus for washing biological material is provided which includes an outer sleeve, and an inner sleeve disposed within the outer sleeve. The outer sleeve has an open end for receiving the biological material, and an opposed closed end. The inner sleeve is detachably and slidably positioned within the outer sleeve, and includes a first port for receiving and dispensing washing liquid, a second port defining a liquid flow path between an interior of the inner sleeve and an interior of the outer sleeve, and a filter disposed in the second port. The filter allows passage of washing liquid but not passage of the biological material therethrough. A chamber, formed between the filter and the closed end of the outer sleeve, is configured to permit flow of washing liquid via the filter while retaining the biological material therein.

19 Claims, 5 Drawing Sheets

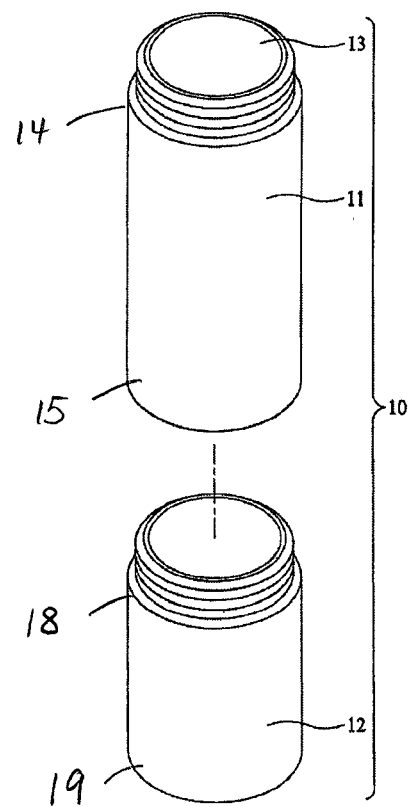
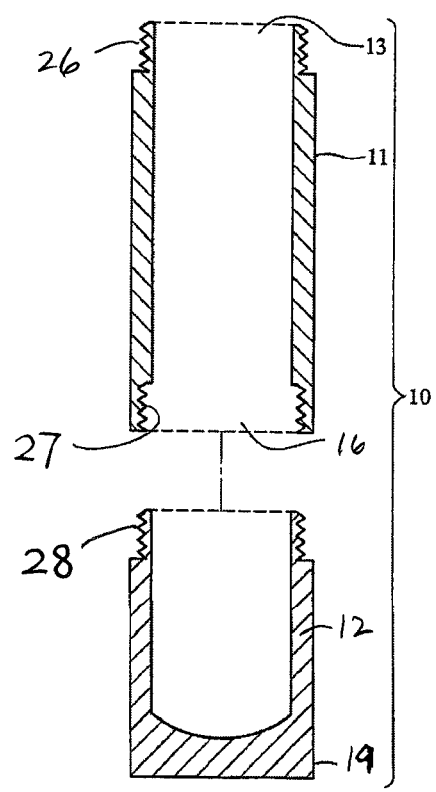
FIG. 2A
FIG. 2B

APPARATUS AND METHOD FOR WASHING BIOLOGICAL MATERIAL

CROSS-REFERENCE TO RELATED APPLICATIONS

This application claims the benefit of Taiwanese Application No. 96123957 filed Jul. 2, 2007. The subject matter of this priority document is incorporated by reference herein.

BACKGROUND

Advances in medical technologies have offered new promises in the field of tissue regeneration. Recently, for example, bioengineered cartilage tissue has been surgically implanted in patients to repair cartilage in injured knees. In some situations, to engineer such an implant, primary cells are harvested from a donor tissue and cultured on scaffolds to form new tissues. During this process, harvested and cultured cells/tissues are frequently washed and filtered to remove chemical reagents and prevent contamination. Conventional washing apparatus include laboratory centrifuges that use centrifugal forces to separate tissue/cell from mixtures. However, laboratory centrifuges are not suitable for use in operating rooms.

SUMMARY

In one aspect, in general, an apparatus for washing biological material is provided which includes an outer sleeve, and an inner sleeve disposed within the outer sleeve. The outer sleeve has an open end for receiving the biological material, and an opposed closed end. The inner sleeve is detachably and slidably positioned within the outer sleeve, and includes a first port for receiving and dispensing washing liquid, a second port defining a liquid flow path between an interior of the inner sleeve and an interior of the outer sleeve, and a filter disposed in the second port. The filter allows passage of washing liquid but not passage of the biological material therethrough. A chamber, formed between the filter and the closed end of the outer sleeve, is configured to permit flow of washing liquid via the filter while retaining the biological material therein.

Embodiments may include one or more of the following features.

The outer sleeve includes a first sleeve piece and a second sleeve piece detachably connected to the first sleeve piece. The inner sleeve includes a resilient member that sealingly engages an inner peripheral surface of the outer sleeve. The resilient member includes an annular rubber member.

The outer sleeve comprises a base member and an extension member. The base member has an open end and an opposed closed end, and the extension member has open, first and second ends which are respectively opposed. The first end of the extension member is configured to detachably connect to the open end of the base member. The second end of the extension member is configured to detachably connect to another extension member.

The first port of the inner sleeve includes a stop portion, the stop portion configured to limit relative axial motion of the inner sleeve with respect to the outer sleeve.

The filter may be removably disposed in the second port. The filter may be a mesh filter having a plurality of mesh openings. The size of the plurality of mesh openings ranges from 100 μm to 3000 μm in diameter. Alternatively, the filter may be a membrane filter having a plurality of membrane openings. The size of the plurality of membrane openings ranges from 5 μm to 20 μm in diameter.

In another aspect, in general, a method of washing biological material is provided. The method includes the following steps: Providing biological material; placing the biological material into a chamber; and driving washing liquid in and out of the chamber through a filter by expanding and contracting the chamber, while retaining the biological material within the chamber.

Embodiments may include one or more of the following additional steps: Providing said washing liquid inside the chamber; discharging said washing liquid from the chamber through the filter; providing fresh washing liquid to the chamber after discharging said washing liquid; agitating the washing liquid within the chamber; and collecting said biological material after discharging said washing liquid.

In some embodiments, the method further includes one or more of the following steps: Providing an outer sleeve having an open end for receiving the biological material and an opposed closed end; and providing an inner sleeve detachably and slidably positioned within the outer sleeve. In some embodiments, the inner sleeve includes a first port for receiving and dispensing said washing liquid, and a second port defining a liquid flow path between an interior of the inner sleeve and an interior of the outer sleeve. In addition, the filter is disposed in the second port, and the chamber is formed between the filter and the closed end of the outer sleeve.

Embodiments may further include the following feature. The outer sleeve includes a first sleeve piece and a second sleeve piece detachably connected to the first sleeve piece, and the method includes the further method step of detaching the first sleeve piece from the second sleeve piece to collect said biological material.

Other features and advantages of the invention are apparent from the following description, and from the claims.

BRIEF DESCRIPTION OF THE DRAWINGS

FIG. 2A is a perspective view of the outer sleeve of the apparatus shown in FIG. 1.

FIG. 2B is a sectional view of the outer sleeve of FIG. 2A.

DETAILED DESCRIPTION

Figure 1:
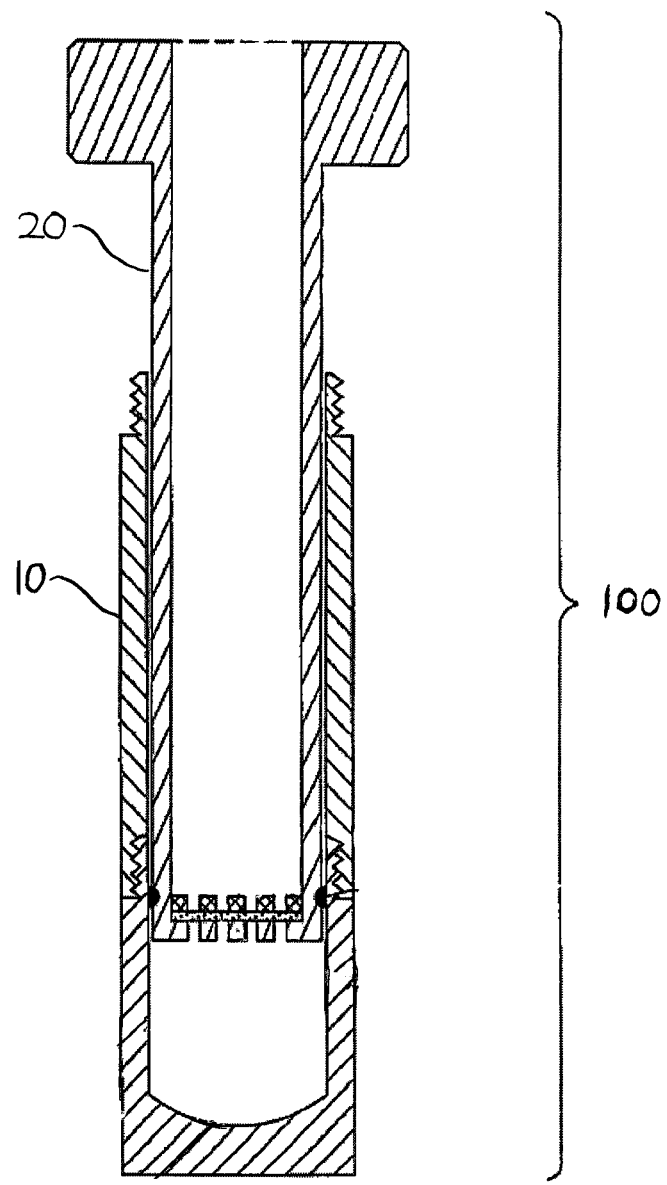
FIG. 1 is a sectional view of an apparatus for washing biological material.

Referring to FIG. 1, in a preferred embodiment, a washing apparatus 100 includes an inner sleeve 20 detachably and slidably positioned in an outer sleeve 10. The inner sleeve 20 and the outer sleeve 10 are elongate tubular members, and in some embodiments are circular in cross section.

Referring to FIGS. 2A and 2B, the outer sleeve 10 includes a first sleeve piece 11 and a second sleeve piece 12. The second sleeve piece 12 serves as a base member, and includes an open upper end 18, and a closed lower end 19. The terms "upper" and "lower" are used here and throughout this document for descriptive purposes rather than to imply any absolute relative orientation. The first sleeve piece 11 serves as an extension member, and includes opposed upper 14 and lower 15 ends. Both the upper and lower ends 14, 15 are open. The opening in the upper end 14 is identified as an opening 13. The lower end 15 of the first sleeve piece 11 is detachably connected to the open upper end 18 of the second sleeve piece 12.

In some embodiments, the first and second sleeve pieces are connected, e.g., by threads, although it is within the scope of the invention to detachably connect the first and second sleeves 11, 12 by other conventional means, such as press-fit engagement. In some embodiments, the outer periphery of the upper end 18 of the second sleeve piece 12 is provided with threads 28 configured to cooperatively engage complementary threads 27 formed on the inner periphery of the lower end 15 of the first sleeve piece 11. In some embodiments, the outer periphery of the upper end 14 of the first sleeve piece is provided with threads 26 configured to cooperatively engage complementary threads of an additional extension member (not shown).

The outer sleeve 10 is configured to receive, through the opening 13, biological material that needs to be washed. When washing is completed, the first sleeve piece 11 can be detached from the second sleeve piece 12 in which the biological material is collected.

Figure 3A:
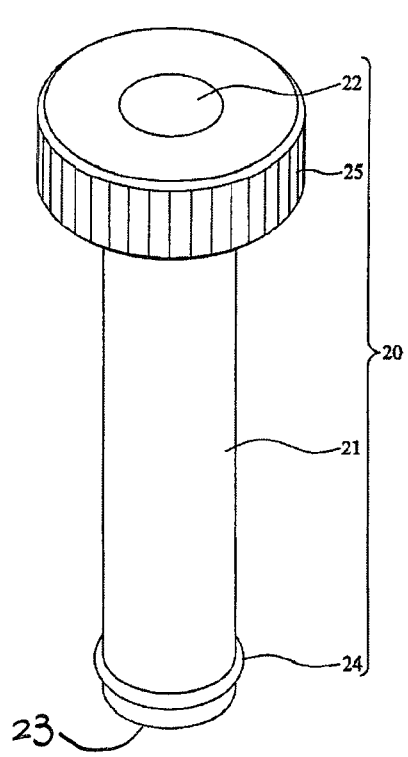
FIG. 3A is a perspective view of the inner sleeve of the apparatus shown in FIG. 1.
Figure 3B:
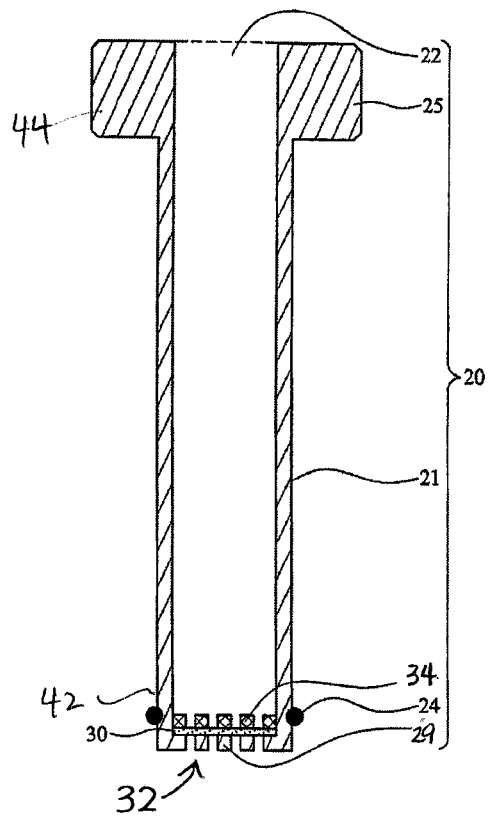
FIG. 3B is a sectional view of the inner sleeve of FIG. 3A.

Referring to FIGS. 3A and 3B, the inner sleeve 20 has a first port 22 formed in an upper end 44 thereof, and a second port 23 formed in a lower end 42 thereof. The first port 22 is configured to receive washing liquid (e.g., saline), while the second port 23 defines a flow path for liquid exchange between the interiors of the inner and outer sleeves 20 and 10. The upper end 44 of the inner sleeve 20 includes a stop member 25. The stop member 25 also serves as a handle.

The stop member 25 is an outwardly extending protrusion having an outer dimension that is greater than the dimension of the opening 13 in the upper end of the outer sleeve 10. The stop member 25 determines a maximum distance that the inner sleeve 20 is allowed to travel within in the outer sleeve 10. The inner sleeve 20 further includes a tubular body 21 extending from the stop member 25. In some embodiments, the tubular body 21 has an axial dimension that is less than that of the outer sleeve 10, so that when the inner sleeve 20 is inserted into the outer sleeve 20 to the extent permitted by the stop member 25, the lower end 42 of the inner sleeve 20 is spaced apart from the closed lower end 19 of the outer sleeve. That is, a chamber 50 is formed within the outer sleeve between the lower end 42 of the inner sleeve 20 and the closed lower end 19 of the outer sleeve, in which the biological material may be collected. Thus, the stop member 25 is provided so as to limit the extent to which the inner sleeve moves relative to the outer sleeve 10, whereby mishandling of the apparatus 100 that may damage the biological material is avoided.

The chamber 50 varies in size based on the relative positions of the inner and outer sleeves 10, 20.

The inner sleeve 20 further includes a filter structure 32 disposed in the second port 23. Thus, an upper boundary of the chamber 50 is provided by the filter structure 32. Biological material 40 can be placed in the outer sleeve 10 and confined in the chamber 50 by the filter 30 during washing process (see FIG. 5A). For purposes of this disclosure, biological material 40 may include, but is not limited to, one or more of cells or lysates thereof, and tissues.

In some embodiments, a resilient member 24 is provided at the lower end 42 of the inner sleeve 20 that sealingly engages an inner peripheral surface of the outer sleeve 10. The resilient member 24 is affixed to the outer peripheral surface of the inner sleeve 20, and may consist of, for example, an annular rubber member (e.g., an o-ring). The resilient member 20 serves to seal the space between the inner peripheral surface of the outer sleeve 10 and the outer peripheral surface of the inner sleeve 20, whereby washing fluid and biological material is prevented from exiting the chamber 50 other than through the filter 30.

Figure 5A:
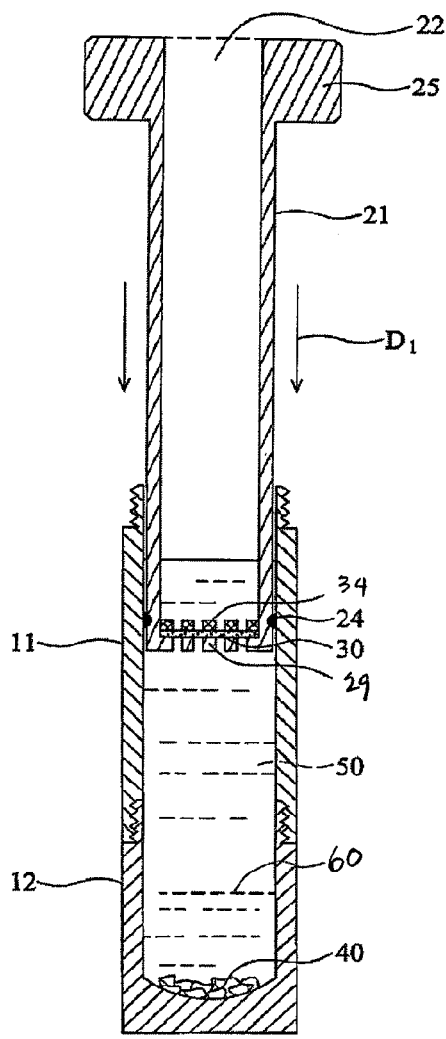
FIGS. 5A and 5B depict exemplary operation modes of the washing apparatus.
Figure 5B:
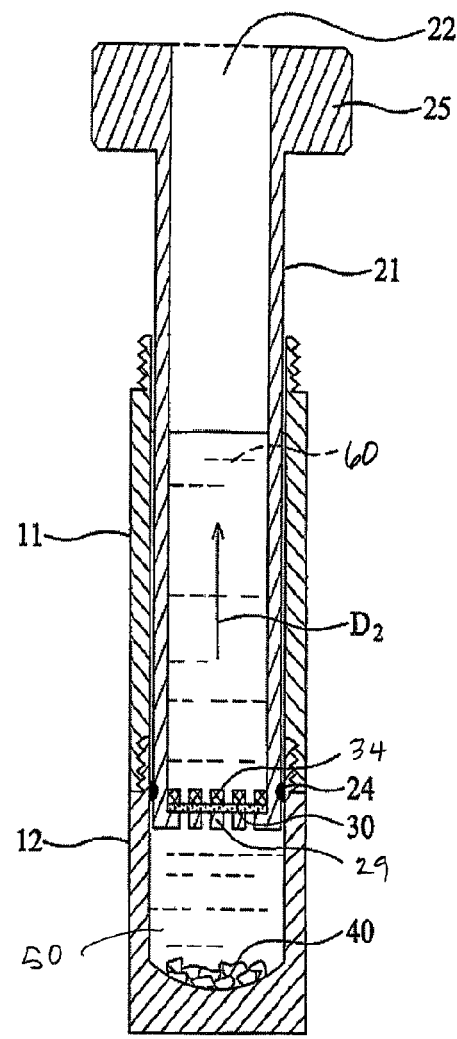

The filter structure 32 disposed in the second port 23 defines a liquid flow path between the interiors of the inner and outer sleeves 20, 10. In some embodiments, the filter structure 32 includes a filter 30 affixed to and sandwiched between a wire mesh member 34 and support members 29 formed in the second port 23 (FIGS. 3B, 5A, and 5B). In other embodiments, the filter structure 32 includes a filter 30 affixed to and sandwiched between two wire mesh members (not shown). This arrangement provides additional support to the filter 30 to prevent filter breakage or deformation during the washing process. In still other embodiments, the filter 30 is mounted on a support structure (e.g., a wire mesh member) that is detachable from the second port 23 to allow reuse of the washing apparatus with replacement filters (not shown).

Depending on the implementation, various filters may be employed in the filter structure 32 of washing apparatus 100. For example, when washing tissues obtained from cartilage, a mesh filter having a pore size of 100 μm may be suitable, while a mesh filter having a pore size in the range from 150 μm to 3000 μm may be suitable for tissues obtained from an umbilical cord. When the biological material to be washed consists of cells rather than tissues, it is preferable to choose membrane filters having a smaller pore size. For example, when washing cells, a membrane filter having a pore size of 10 μm may be suitable. In some embodiments, the membrane filters may include pore sizes in the range of 5 μm to 20 μm.

Figure 4:
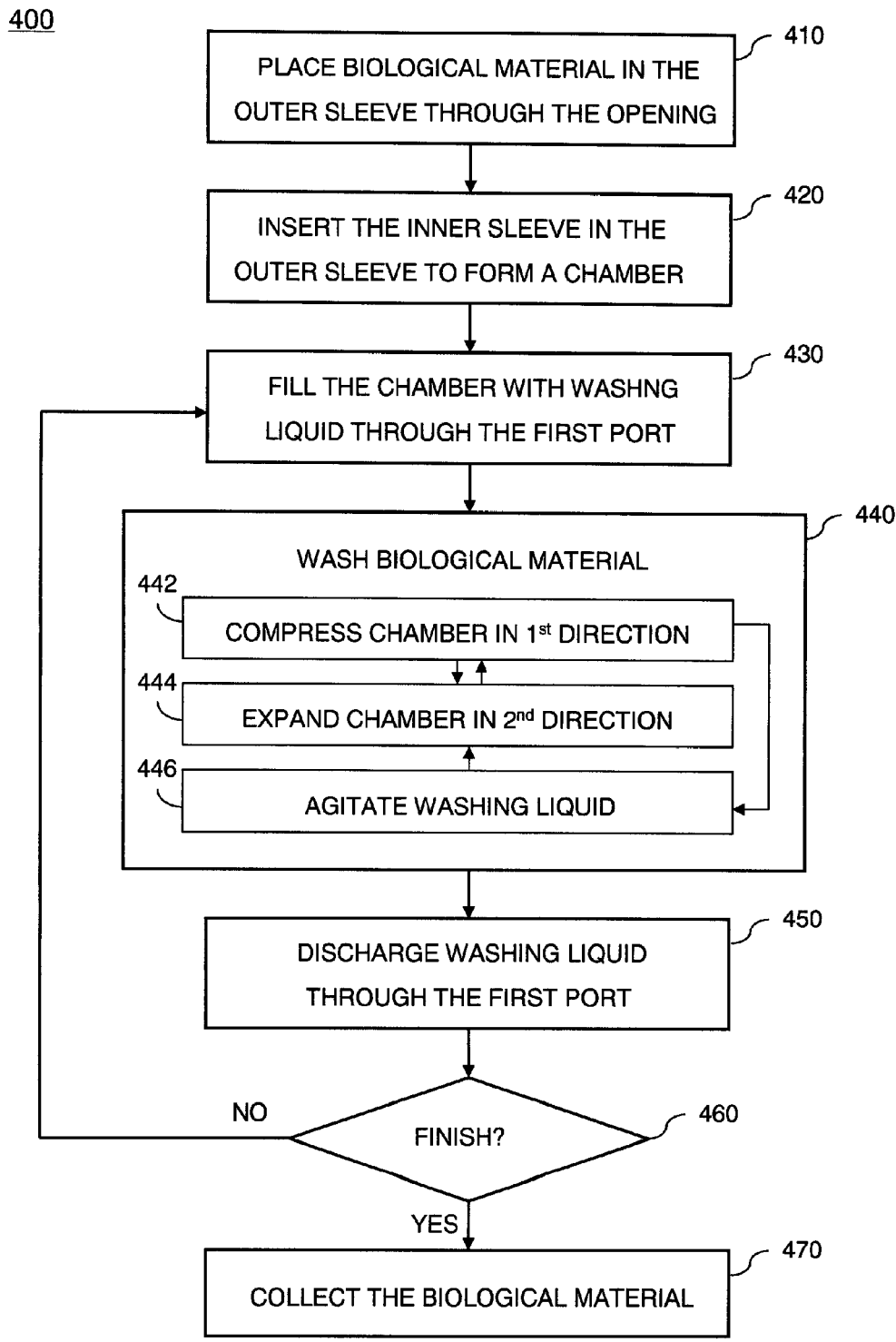
FIG. 4 is a flow chart illustrating a method of washing biological material using the apparatus shown in FIG. 1.

Referring to FIG. 4, a flow chart 400 illustrates a method of washing biological material using the apparatus 100 described above.

Initially, in step 410, biological material 40 (e.g., biological tissue) is placed in the outer sleeve 10 through the opening 13. In step 420, the inner sleeve 20 is inserted in the outer sleeve 10 to form the chamber 50, in which the biological material 40 is retained during the washing process. In step 430, the chamber 50 is filled with washing liquid 60 suitable for this biological material 40. The washing liquid 60 is provided through the first port 22 of the inner sleeve 20. One example of a commonly used washing liquid 60 includes phosphate buffer saline (PBS), but the invention is not limited thereto.

Next, the washing process 440 is performed by driving washing liquid 60 in and out of the chamber 50 through the filter 30. This process 440 includes e.g., moving the inner sleeve 20 in a first axial direction D1 to compress the chamber 50 (step 442), and moving the inner sleeve 20 in a second axial direction D2 to expand the chamber (step 444), as depicted in FIGS. 5A and 5B, respectively. These two steps can be performed multiple times in an alternating manner to remove, for example, undesired chemical reagents contained in the biological material. In some applications, gentle agitation of the mixture (step 446) also helps improve washing efficiency. Gentle agitation may be provided after one or both of the compression step (step 442) or the expansion step (step 444).

During washing, the biological material 40 is substantially retained in the chamber 50, while washing liquid 60 enters and exits the chamber 50 through the filter 30. The rubber resilient member 24, affixed at the exterior of the inner sleeve 20, prevents fluid exchange between inner and outer sleeves 20, 10 other than through the liquid flow path provided by the filter 30.

After the washing process 440, washing liquid 60 in the chamber 50 is discharged through the filter 30 and subsequently the first port 22 to a waste container, as shown in step 450. Discharge of the washing liquid 60 may be achieved, for example, by inverting the apparatus 100.

In some applications, it is desirable to wash the biological material 40 multiple times to ensure successful removal of chemical reagents and other undesired substances. In these cases, after discharging the washing liquid 60 (step 450), fresh washing liquid 60' is supplied to the chamber 50 through the first port 22 (step 430) to repeat the washing process 440 and the discharging step 450.

When biological material 40 has been sufficiently washed (step 460), the inner sleeve 20 is detached from the outer sleeve 10 where the biological material 40 is collected (step 470). In some applications, the first and second sleeve pieces 11 and 12 are further disassembled to provide easy access to the biological material 40.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An apparatus for washing biological material, comprising:
    an outer sleeve including:
        a base member having an open end, and an opposed closed end; and
        an extension member having open, opposed first and second ends, wherein the first end is configured to detachably connect to the open end of the base member and the second end is configured to receive the biological material; and
    an inner sleeve detachably and slidably positioned within the outer sleeve through the open second end of the extension member, the inner sleeve including:
        a first port for receiving and dispensing washing liquid;
        a second port defining a liquid flow path between an interior of the inner sleeve and an interior of the outer sleeve; and
        a filter disposed in the second port, the filter being sandwiched between a wire mesh member and support members and allowing passage of washing liquid but not passage of the biological material therethrough;
    wherein a chamber, formed between the filter and the closed end of the outer sleeve, is configured to permit flow of washing liquid via the filter while retaining the biological material therein.

2. The apparatus of claim 1, wherein the inner sleeve includes a resilient member that sealingly engages an inner peripheral surface of the outer sleeve.

3. The apparatus of claim 1, wherein the second end of the extension member is configured to detachably connect to another extension member.

4. The apparatus of claim 3, wherein the inner sleeve includes a resilient member that sealingly engages an inner peripheral surface of the outer sleeve.

5. The apparatus of claim 4, wherein the resilient member includes an annular rubber member.

6. The apparatus of claim 4, wherein the first port of the inner sleeve includes a stop portion, the stop portion configured to limit relative axial motion of the inner sleeve with respect to the outer sleeve.

7. The apparatus of claim 6, wherein the filter is removably disposed in the second port.

8. The apparatus of claim 1, wherein the first port of the inner sleeve includes a stop portion, the stop portion configured to limit relative axial motion of the inner sleeve with respect to the outer sleeve.

9. The apparatus of claim 1, wherein the filter is removably disposed in the second port.

10. The apparatus of claim 1, wherein the filter is a mesh filter having a plurality of mesh openings.

11. The apparatus of claim 10, wherein the size of the plurality of mesh openings ranges from 100 µm to 3000 µm in diameter.

12. The apparatus of claim 1, wherein the filter is a membrane filter having a plurality of membrane openings.

13. The apparatus of claim 12, wherein the size of the plurality of membrane openings ranges from 5 µm to 20 µm in diameter.

14. A method of washing biological material, the method comprising:
    providing an apparatus including:
        (a) an outer sleeve having (i) a base member having an open end, and an opposed closed end; and (ii) an extension member having open, opposed first and second ends, wherein the first end is configured to detachably connect to the open end of the base member and the second end is configured to receive the biological material; and
        (b) an inner sleeve detachably and slidably positioned within the outer sleeve through the open second end of the extension member, the inner sleeve including: (i) a first port for receiving and dispensing washing liquid; (ii) a second port defining a liquid flow path between an interior of the inner sleeve and an interior of the outer sleeve; and (iii) a filter disposed in the second port, the filter being sandwiched between a wire mesh member and support members and allowing passage of washing liquid but not passage of the biological material therethrough;
        (c) a chamber containing a washing liquid and the biological material, wherein the chamber is formed between the filter and the closed end of the outer sleeve and configured to permit flow of washing liquid via the filter while retaining the biological material therein; and
    driving the washing liquid in and out of the chamber through the filter by expanding and contracting the chamber, while retaining the biological material within the chamber.

15. The method of claim 14, further comprising the step of discharging said washing liquid from the chamber through the filter.

16. The method of claim 15, further comprising the step of providing fresh washing liquid to the chamber after discharging said washing liquid.

17. The method of claim 14, further comprising the step of agitating said washing liquid within the chamber.

18. The method of claim 15, further comprising the step of collecting said biological material after discharging said washing liquid.

19. The method of claim 18, wherein the biological material is collected by detaching the inner sleeve from the outer sleeve.

* * * * *